United States Patent
Burgo

(10) Patent No.: US 11,207,249 B2
(45) Date of Patent: Dec. 28, 2021

(54) NON-PETROCHEMICALLY DERIVED CATIONIC EMULSIFIERS AND RELATED COMPOSITIONS AND METHODS

(71) Applicant: Inolex Investment Corporation, Wilmington, DE (US)

(72) Inventor: Rocco Burgo, Mullica Hill, NJ (US)

(73) Assignee: INOLEX INVESTMENT CORPORATION, Wilmington, DE (US)

( * ) Notice: Subject to any disclaimer, the term of this patent is extended or adjusted under 35 U.S.C. 154(b) by 165 days.

(21) Appl. No.: 15/864,887

(22) Filed: Jan. 8, 2018

(65) Prior Publication Data

US 2018/0193233 A1 Jul. 12, 2018

Related U.S. Application Data

(63) Continuation of application No. 14/709,344, filed on May 11, 2015, now abandoned.

(60) Provisional application No. 61/990,983, filed on May 9, 2014.

(51) Int. Cl.
| | |
|---|---|
| *A61K 8/06* | (2006.01) |
| *A61K 8/44* | (2006.01) |
| *A61Q 19/00* | (2006.01) |
| *C07C 229/08* | (2006.01) |
| *A61Q 5/00* | (2006.01) |

(52) U.S. Cl.
CPC ............ *A61K 8/06* (2013.01); *A61K 8/44* (2013.01); *A61Q 5/00* (2013.01); *A61Q 19/00* (2013.01); *C07C 229/08* (2013.01); *A61K 2800/10* (2013.01)

(58) Field of Classification Search
CPC ........ A61K 2800/10; A61K 8/06; A61K 8/44; A61Q 19/00; C07C 229/08
See application file for complete search history.

(56) References Cited

U.S. PATENT DOCUMENTS

| | | | |
|---|---|---|---|
| 3,937,811 A | 2/1976 | Papantoniou et al. | |
| 4,216,227 A | 8/1980 | Cook et al. | |
| 4,323,694 A | 4/1982 | Scala, Jr. | |
| 5,560,917 A | 10/1996 | Cohen et al. | |
| 8,039,010 B2 | 10/2011 | Trogden et al. | |
| 8,105,569 B2 | 1/2012 | Burgo | |
| 8,287,844 B2 | 10/2012 | Burgo et al. | |
| 2005/0013839 A1 | 1/2005 | Yamamoto et al. | |
| 2011/0274641 A1* | 11/2011 | Burgo ..................... | A61K 8/44 424/70.14 |

FOREIGN PATENT DOCUMENTS

| | | |
|---|---|---|
| CN | 102549138 A | 7/2012 |
| EP | 0847987 A1 | 6/1998 |
| FR | 2983403 A1 | 6/2013 |
| JP | 10168044 H | 6/1998 |
| JP | 2012532108 A | 12/2012 |
| WO | 2003105806 A1 | 12/2003 |
| WO | 2012172207 A2 | 12/2012 |
| WO | 2013150044 A2 | 10/2013 |

OTHER PUBLICATIONS https://www.sigmaaldrich.com/life-science/metabolomics/learning-center/amino-acid-reference-chart.html by Millipore Sigma accessed on Nov. 5, 2020 (Year: 2020).*
https://www.chemicalbook.com/ChemicalProductProperty_EN_CB4780292.htmhttps://www.chemicalbook.com/ChemicalProductProperty_EN_CB4780292.htm by Chemical Book, accessed on Nov. 5, 2020. (Year: 2020).*
International Search Report, Intl. Publ. No. PCT/US2015/030215, dated Aug. 5, 2015, 4 pages.
International Preliminary Report on Patentability, Intl. Publ. No. PCT/US2015/030215, dated Nov. 15, 2016, 13 pages.
Decision to Grant a Patent from Japanese Patent Office for JP Application No. 2016-567018; dated Apr. 21, 2021, 2 pages.

* cited by examiner

*Primary Examiner* — Jean P Cornet
(74) *Attorney, Agent, or Firm* — Cozen O'Connor

(57) ABSTRACT

The invention includes a neutralized amino acid ester emulsifier, emulsions and compositions containing the emulsifier, and related methods. The emulsifier is a neutralized amino acid ester that is a reaction product of a neutral amino acid with a fatty alcohol and is represented by formula (I):

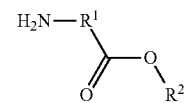

wherein $R^1$ is an alkyl group that has 6 to 24 carbon atoms; $R^2$ is an alkyl group that has 6 to 36 carbon atoms; and the amine group of the amino acid is neutralized with an acid. The emulsifier is cationic. Also included are stable emulsions and compositions, preferably personal care compositions, that include the emulsifier and which may have pH levels of 5.5 or greater. Encompassed within the scope of the invention are methods of increasing the substantivity of a composition to a negatively charged substrate using the emulsifier, methods of emulsifying and methods of preparing a personal care composition using the emulsifier.

8 Claims, 9 Drawing Sheets

NON-PETROCHEMICALLY DERIVED CATIONIC EMULSIFIERS AND RELATED COMPOSITIONS AND METHODS

CROSS REFERENCE TO RELATED APPLICATION

This application is a continuation of U.S. non-provisional Ser. No. 14/709,344, filed May 11, 2015 which claims the benefit under 35 U.S.C. § 119(e) to U.S. Provisional Patent Application No. 61/990,983, filed May 9, 2014, each entitled "Non-Petrochemically Derived Cationic Emulsifiers and Related Compositions and Methods," and the disclosures of each of which are hereby incorporated by reference in their entireties.

BACKGROUND OF THE INVENTION

Sales of "natural" products within the personal care industry continue to show significant growth. Popular culture has driven this growth by popularizing the idea that there may be potential adverse effects to the body (toxicity) and to the environment (pollution, hastening of climate change, and environmental toxicity) associated with the use of ingredients derived from fossil fuels. The personal care industry has rapidly advanced its attempts to identify ingredients described as "renewable" and "sustainable," that is, ingredients of non-fossil fuel origin for use in the formulation of virtually all cosmetic product types and forms.

In many instances, the industry has successfully identified replacements for many ingredients that are historically of fossil fuel origin Examples of this are the replacement of mineral oils, silicones, and petrochemically-derived synthetic esters with vegetable oils and natural esters, synthetic fragrances with essential oils, and petrochemical preservatives with certain extracts.

Although used in marketing materials, the term "natural" has not yet been completely defined. However, efforts are underway by industry trade organizations to give the term a more concise and consistent meaning Historically, it has been generally recognized that materials derived from renewable and/or sustainable, or otherwise non-fossil fuel sources are considered "natural" by the marketplace. More recently the definition of "natural" has been further refined. For example, there is a trend within the trade to prohibit animal-derived materials and plant-derived materials that are obtained from the use of genetically-modified organisms (GMO) from use in natural products.

Also, certain chemical processes used in the manufacture of ingredients, especially those processes that employ petrochemical solvents, generate unrecoverable waste, and/or consume excessive resources, are frowned upon or may otherwise be prohibited. The use of "Green Chemistry" principles in the production of cosmetic and personal care ingredients is rapidly becoming a positive benefit that can be exploited in the marketing of products produced using those principles. Thus, the evolving definition of "natural" currently includes products that are not petrochemically derived. However, the other concepts discussed above (non-animal, non-GMO, Green Chemistry) may be taken into consideration when creating "natural" products, and to satisfy market demands.

One particular challenge facing formulators of natural products relates to the identification of suitable emulsifiers. An emulsifier is a type of surfactant typically used to keep emulsions (metastable mixtures of immiscible fluids) well dispersed. Emulsifiers typically have a hydrophobic (water-fearing) and a hydrophilic (water-loving) moiety. In an emulsion involving an oil and water, emulsifiers will surround the oil with their hydrophobic moiety oriented toward the oil, thus forming a protective layer so that the oil molecules cannot coalesce. This action helps keep the dispersed phase in small particles and preserves the emulsion. Emulsifiers may be anionic, nonionic, or cationic.

An emulsifier for use in a personal care product is one that will maintain consistent emulsion characteristics within the composition, such as particle size, appearance, texture, and viscosity, substantially constant for as long a period as possible since all emulsions due to their metastable nature will eventually separate into their constituent oil soluble and water soluble components. Stability of the emulsion is highly desirable in most products, since among other advantages, this stability contributes to an extended shelf life of the product and the maintenance of its initial aesthetic properties over time.

Although the vast majority of emulsifiers currently used personal care products are wholly or partially petrochemically derived such as polyethylene glycol (PEG) derivatives and amine quaternaries, a limited number of known emulsifiers may meet the current definition of natural. However, presently available "natural" emulsifiers are either nonionic or anionic emulsifiers. The natural, nonionic emulsifiers are typically (i) partial esters of long chain fatty acids with a polyol, such as for example, long chain partial esters of sugars and of polyglycerols, or (ii) alkylpolyglucosides. Although these nonionic emulsifiers can be effective in building stable emulsions, they are mono-functional. That is, they do not provide any other significant formulation or aesthetic/skinfeel advantages to the composition. Specifically, unlike cationic emulsifiers, they do little or nothing to provide any conditioning and/or aesthetic benefits to the hair or skin because they are not substantive to these substrates, which are negatively charged.

The natural, anionic emulsifiers are typically the long chain fatty acid soaps of fatty acids and sulfuric acid esters (sulfates) of fatty alcohols. These tend to be drying to the skin and provide no aesthetic or conditioning benefits because, like the hair and skin, they are negatively charged and therefore tend to be repelled by these substrates Thus, like the natural nonionic emulsifiers, they are essentially monofunctional from a formulator's perspective.

Cationic emulsifiers are advantageous from a formulator's perspective, as they are capable of providing more than one function or benefit to an end formulation. The ability to obtain one or more benefits from one material conserves resources in formulation and production, specifically, the amount of time, power, labor, money and supply chain logistics required is potentially reduced.

Currently there are few cationic emulsifiers that can be marketed as "natural". Many personal care applications require or are improved by the use of cationic emulsifiers. Owing to the fact that typical cationic emulsifiers are built from a long chain (hydrophobic) alkyl group attached to a hydrophilic moiety, they act as emulsifiers much the same way as the nonionic and anionic emulsifiers previously described. However, in a cationic emulsifier, the hydrophilic portion of the molecule is positively charged. This cationic moiety will electrostatically bind to (i.e., be substantive to) negatively charged substrates such as the hair and skin. The hydrophobic moiety, which is nonionic, has no affinity for the substrate, and will orient away from the substrate creating a protective layer of fatty material that can provide enhanced sensory properties to the skin and nails.

As noted above, the capability of a cationic emulsifier to act as an emulsifier and provide other benefits in a given composition is advantageous. Specifically, the property of substantivity is provided by cationic emulsifiers and differentiates them from anionic and/or nonionic emulsifiers. It is substantivity that facilitates the conditioning benefits of the end product. Therefore, in addition to being emulsifiers, cationic emulsifiers improve the aesthetics of formulations that include them, and allow the formulation of personal care products that can condition, moisturize, and repair the skin, hair, or nails.

Cationic emulsifiers, when used in hair care applications such as cream conditioners, may provide excellent conditioning benefits such as improvement in the aesthetics of the composition when applied, creaminess and richness of the conditioner/moisturizer, and improvements in such application properties as softening, anti-static behavior, fly-away, wet combing, and dry combing. When cationic emulsifiers, are used in skin care preparations, they are known to provide what is known in the industry as a "dry, light, powdery" skin feel that is a distinct advantage in many skin care products Exemplary traditional cationic emulsifiers that exhibit these properties include quaternized cationic emulsifiers such as cetrimonium chloride, behentrimonium chloride and distearyldimonium chloride, and amidoamines such as stearamidopropyl dimethylamine and behenamidopropyl dimethylamine.

Prior art natural cationic emulsifiers are described in U.S. Pat. Nos. 8,287,844 B2 and 8,105,569 (collectively "the Burgo Art") In the Burgo Art, the cationic emulsifier is derived from a neutralized α-amino acid, preferred to be leucine or isoleucine. The emulsifiers of the Burgo Art are reported as useful in increasing the substantively of personal care products. However, these cationic emulsifiers are most effective at acidic pHs and are less effective at higher, more neutral pHs (e.g., 5.5 and above). Since many personal care compositions are formulated at theses higher pHs, the emulsifier of the Burgo Art may not be a favored option in a variety of personal care formulations, such as those designed for babies or for people with sensitive skin.

Accordingly, there is a need in the art for natural cationic emulsifiers that are capable of facilitating a stable emulsion, have performance characteristics, use characteristics and substantivity similar to the traditional, non-natural, cationic emulsifiers, and which maintain their performance characteristics at higher pH values.

BRIEF SUMMARY OF THE INVENTION

The invention includes emulsions and compositions, such as personal care compositions, containing a cationic neutralized amino acid ester emulsifier. The emulsifier is natural, and in some embodiments, the emulsions and compositions may be as well. The compositions of the invention exhibit performance characteristics (such as substantivity to skin and hair, shelf stability and conditioning/lubrication capabilities) comparable to compositions containing petrochemicals and/or derivatives of petrochemicals, and/or superior to those exhibited by other non-petrochemical containing compositions. The emulsifier is particularly suitable for use in compositions having a final pH of, for example, about 5 to about 8.5 or o about 9.3, as it maintains its performance characteristics at these pHs.

The invention includes a neutralized amino acid ester emulsifier, emulsions and compositions containing the emulsifier, and related methods. The emulsifier is a neutralized amino acid ester that is a reaction product of a neutral amino acid with a fatty alcohol and is represented by formula (I):

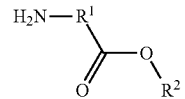

wherein $R^1$ is an alkyl group that has 6 to 24 carbon atoms; $R^2$ is an alkyl group that has 6 to 36 carbon atoms, and the amine group of the amino acid is neutralized with an acid. The emulsifier is cationic. Also included are stable emulsions and compositions, preferably personal care compositions, that include the emulsifier and which may have pH levels of 5.5 or greater.

Encompassed within the scope of the invention are methods of increasing the substantivity of a composition to a negatively charged substrate using the emulsifier, methods of emulsifying and methods of preparing a personal care composition using the emulsifier.

BRIEF DESCRIPTION OF THE DRAWINGS

The foregoing summary as well as the following detailed description of preferred embodiments of the invention will be better understood when read in conjunction with the appended drawings. The invention is not limited to the precise arrangements and instrumentalities shown. In the drawings.

DETAILED DESCRIPTION OF THE INVENTION

Figure 1:
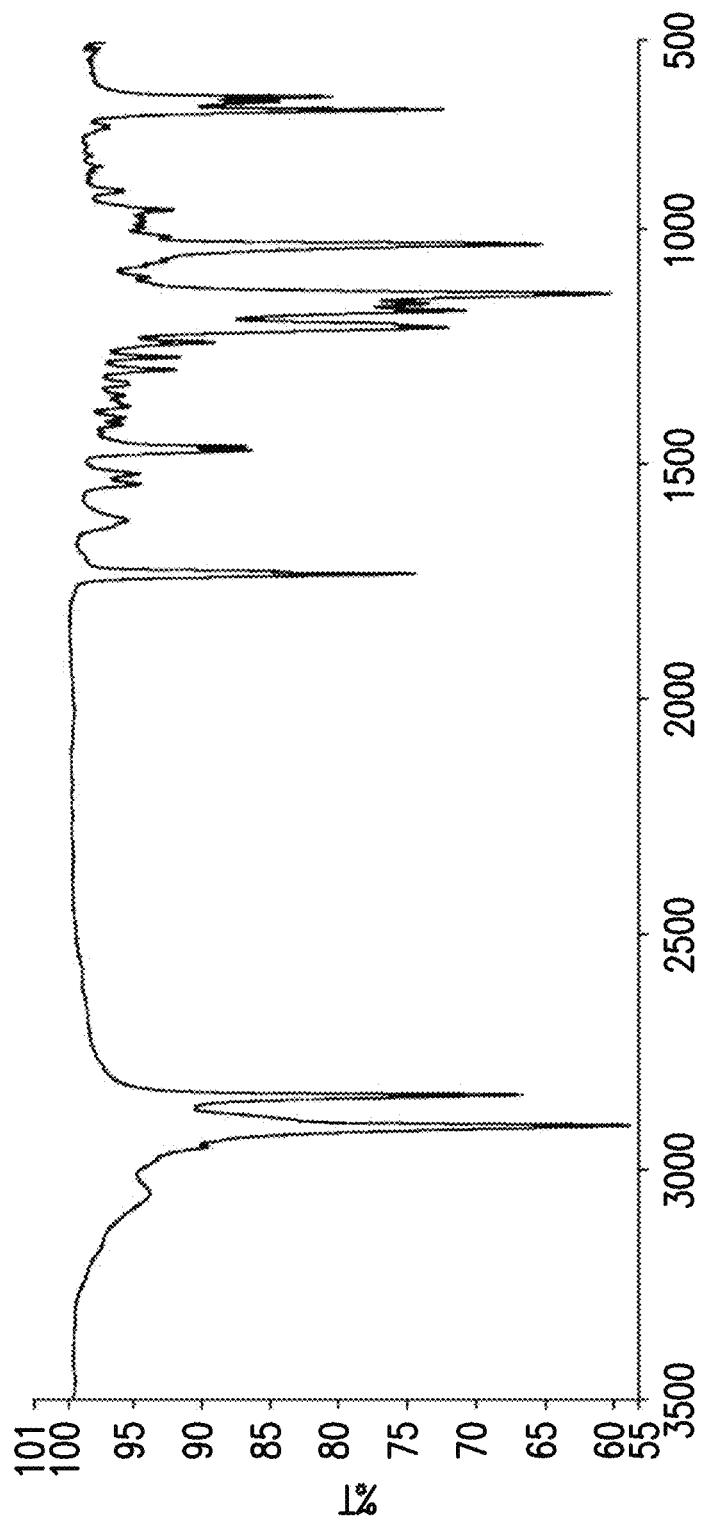
FIG. 1 is an infrared spectrum of an embodiment of the emulsifier of the invention (BAE)

The invention includes neutralized amino acid ester cationic emulsifiers as described herein, compositions containing the inventive emulsifier and methods that utilize it to emulsify and/or increase the substantivity of a formulation. The emulsifier is "natural". The adjective "natural" as used herein means that the material being described as such falls into at least one the following categories: it is not derived from petrochemical materials; it is produced from non-animal derived reactants; it is produced from non-GMO reactants; and/or it is prepared by processes that utilize Green Chemistry principles. In an embodiment, the emulsifier is included in a composition that contains no other components that are not "natural", although it can also be used effectively in compositions that contain one or more non-natural ingredients.

The emulsifier of the invention may also be used as an additive in compositions that are not emulsions and/or do not require emulsification to increase the substantivity of the composition to a negatively charged substrate. For convenience, the term "emulsifier" referring to the compound of the invention is used throughout the specification. However, any description, identification, process, example, etc that is applied to the "emulsifier" of the invention may also apply to/be descriptive of the compound of the invention when it is used as an additive in a non-emulsion.

In some embodiments, the emulsifier of the invention can be used in an anyhydrous composition (such as an anhydrous gel) as an additive to increase substantivity of the gel to a negatively charged substrate. It can be used in compositions having a first phase, and to which a second phase is subsequently added by an end user. For example, a hair treatment may be sold by a beauty supply house in the form of a non-aqueous gel containing the emulsifier of the invention to a hairdresser. Before use on a client's hair, the hairdresser may add an aqueous phase to the composition and form an emulsion. Alternatively, in some embodiments, the composition may be substantially free of liquid, for example, a powder, to which water or another solvent or mixture of solvents (aqueous and non-aqueous) may be added by the end user.

When used in a emulsion composition, the emulsifier of the invention is capable of increasing the kinetic stability of an emulsion, maintaining consistent emulsion characteristics over a period of time, such as, for example, particle size, appearance, texture, and viscosity. For example, depending on the specific composition, in some embodiments the emulsifier of the invention is capable stabilizing an emulsion for about 3 months to about 40 months, preferably up to about 36 months. By "stabilizes", it is meant that use of the emulsifier prevents significant observable changes in texture, appearance and/or viscosity over the selected time period. The emulsion may be formed from a first phase and a second phase, or more. The phases may be aqueous and non-aqueous.

The emulsifier of the invention has a cationic structure that makes it suited for personal care compositions, particularly for compositions used in the conditioning of hair and skin, which are negatively charged substrates. In addition, when formulated into a personal care composition, the emulsifiers of the invention exhibit the performance characteristics provided by conventional, non-natural cationic emulsifiers and expected by the consumer, particularly with respect to substantivity, skin feel, and shelf stability. These performance characteristics are maintained even at the higher pHs at which many personal care compositions are formulated.

For example, emulsifiers of the invention maintain their performance properties when incorporated into composition having higher pH values, such as, for example, pHs of about 5.5 to about 7.5, of about 6.0 to about 9.3, or about 6.5 to about 8.5 or about 7.0 to about 8.5. It is believed that this surprising result identified by the inventor is a consequence of the relative distance between the amine and the carbonyl groups on the emulsifier molecule. In the absence of charge 'interference' from the carbonyl group which may occur in an α-amino acid based structure, the amine group remains fully protonated at higher pH values and is read by the composition as being more neutral at such pH values than, for example, the brassicyl isoleucinate esylate emulsifier of U.S. Pat. Nos. 8,287,844 B2 and 8,105,569 (collectively, the Burgo Art), the contents of each of which are incorporated herein by reference.

The emulsifier of the invention is substantive (adheres to) negatively charged substrates, and accordingly increases the substantivity to negatively charged substrates of any composition to which it is added Negatively charged substrates include hair, skin, and nails. Other substrates can include leathers, textiles, polymers, polymer coated surfaces, wood, fur, hooves, claws, enamel, porcelain, etc. as long as the surface is or has been treated/modified to have a negative charge.

The inventive neutralized amino acid ester emulsifier of the invention is derived from the esterification of (i) a neutral amino acid having an amine group that has been neutralized with an acid; with (ii) a fatty alcohol. In an embodiment, the amino acid ester of the invention may be represented by the structure of Formula (I):

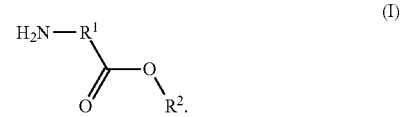

In Formula (I), $R^1$ represents an alkyl group which may be branched or linear, substituted or unsubstituted. In an embodiment, it may be preferred that $R^1$ may have one to 6 to 24 carbon atoms. In some embodiments, $R^1$ may have 6, 7, 8, 9, 10, 11, 12, 13, 14, 15, 16, 17, 18, 19, 20, 21, 22, 23, or 24 carbon atoms. In an embodiment, $R^1$ may be an alkyl group having 11 carbon atoms.

$R^2$ independently represents an alkyl group, which may be linear or branched. In some embodiments, it may contain 6 to 36 carbon atoms. In some embodiments, $R^2$ may have 6, 7, 8, 9, 10, 11, 12, 13, 14, 15, 16, 17, 18, 19, 20, 21, 22, 23, 24, 25, 26, 27, 28, 28, 30, 31, 32, 33, 34, 35, or 36 carbon atoms.

In either of $R^1$ or $R^2$, the carbons of the alkyl groups may independently each have at least one unsaturated carbon atom; in some embodiments, all the carbon atoms are unsaturated.

The amino acid is neutral, one or more different types of neutral amino acids may be used. By "neutral amino acid" it is meant an amino acid that has an equal quantity of carboxcylic acid groups and amine groups. Isoleucine, for example, falls within in this definition. "Neutral amino acids," as such term is used herein, do not include acids having a greater number of carboxcylic acid groups than amine groups or vice versa (the number of amine groups is greater than the number of carboxcylic acid groups).

It may be preferred that the selected amino acid is natural. In some embodiments it is preferred that the amino acid is not derived from animal sources. In an embodiment, it may be preferred that the amino acid(s) are synthetic (laboratory-made) and/or derived from plants, algae, non-animal organisms, non-vertebrate organisms, and/or non-chordate organisms. In an embodiment, the amino acid may be obtained, for example, from vegetable matter by a fermentation process.

To obtain the ester emulsifier of the invention, the amine group of the amino acid is neutralized with an acid. To ensure that all the amine groups in a particular sample are neutralized, it may be preferred that the neutralization reaction is carried out using a stoichiometric excess of a strong acid, to prepare a neutralized amino acid (e.g., on having all of its amino groups neutralized).

To accomplish neutralization, any acid may be used, including organic and inorganic acids. Strong acids may be preferred. Suitable acids include, without limitation, mineral acids, amino acids, hydrochloric acid, phosphoric acid, sulfuric acid, boric acid, and nitric acid. Suitable organic acids may be citric acid, ethanesulfonic acid, acetic acid, formic acid, and oxalic acid. Suitable amino acids may include glutamic acid and aspartic acid. In an embodiment, one may prefer ethanesulfonic acid that is derived from non-GMO ethanol.

Subsequently, the neutralized amino acid is reacted with a fatty alcohol. Suitable fatty alcohols may be linear and/or branched and may additionally be saturated and/or unsaturated. It may be preferred that the fatty alcohol contains 6 to 36 carbon atoms.

Examples of suitable fatty alcohols may include, without limitation, lauryl alcohol, myristyl alcohol, palmityl alcohol, stearyl alcohol, oleyl alcohol, isostearyl alcohol, octyldodecanol, arachidyl alcohol, behenyl alcohol and mixtures or combinations thereof.

Other fatty alcohols may include 3-methyl-3 pentanol, ethchlorvynol, 1-octanol, 2-ethyl hexanol, 1-nonanol, undecanol, tridecanol, pentadecyl alcohol, palmitoleyl alcohol, heptadecyl alcohol, nonadecyl alcohol, Heneicosyl alcohol, erucyl alcohol, ceryl alcohol, 1-hepracosanol, cluytyl alcohol, 1-nonacosanol, myricyl alcohol, 1-dotriacontanol, and geddyl alcohol Any mixture of two or more fatty alcohols may be used.

In some embodiments, it may be desirable that the fatty alcohols are derived from non-petrochemical sources, preferably renewable vegetable sources. Without limitation, examples may include be *Brassica* alcohol, rapeseed, palm, coconut or jojoba oils or a mixture of these or others. *Brassica* alcohol is the fatty alcohol derived from *Brassica* oil. In some embodiments, the *Brassica* alcohol selected may be derived from hydrogenated high erucic acid rapeseed (HEAR) oil, and may be a mixture of straight chain saturated fatty alcohols such as palmityl ($C_{16}$), stearyl ($C_{18}$), arachidyl ($C_{20}$), and behenyl ($C_{22}$) alcohols. The typical weight percentages of each alcohol in the fatty alcohol mixture may be about 3 wt. % palmitic, about 40 wt % stearyl, about 10 wt. % arachidyl, and about 47 wt. % behenyl. These percentages can vary based upon seasonality, and varietal of rapeseed oil used as the parent vegetable source.

In an embodiment, the esylate is prepared by reacting the amine group on the amino acid with an acid, for example, ethanesulfonic acid, prior to esterification. However, the neutralized amino acid ester of the invention may be synthesized by any methods commonly known or developed in the art.

Exemplary preferred neutralized amino acid esters within the scope of the invention ("the esylates") may be octyldodecyl aminolaurate esylate (OAE), brassicyl aminolaurate esylate (BAE) and isostearyl aminolaurate esylate (IAE). OAE may be derived from the esteritication of octylododecyl alcohol with 12-aminolauric esylate. BAE may be derived from the esterification of *Brassica* alcohol with 12-aminolauric esylate. IAE may be derived from the esterification of isostearyl alcohol and 12-aminolauric esylate.

The emulsifiers of the invention may be incorporated into a composition, preferably personal care compositions, containing ingredients that are immiscible to create and maintain or to help maintain an emulsion. For example, in a composition containing an aqueous phase and a non-aqueous phase, the emulsifier of the invention may be used in an amount sufficient to create a stable emulsion ("effective amount") in the particular composition. As will be understood, the amount required to emulsify a given composition will vary depending on the contents of the composition, but determination of the amount is well within the purview of a person skilled in the art.

In an "average" personal care composition, this amount may be about 1% to about 5% or 2% to about 10% of the weight of the total composition. Of course, greater amounts may also be included, if desired. Preferably, the compositions into which the emulsifier is included are natural, that is, substantially free of petrochemicals, petrochemical derivatives, materials derived from genetically modified organisms (such as GMO plant materials), and/or any animal materials or derivatives. By "substantially free", it is meant that none of the materials added to the personal care composition are petrochemicals, petrochemical derivatives, materials derived from genetically modified organisms (such as GMO plant materials), and/or any animal materials or derivatives, although residual amounts of such materials may be present as an artifact of processing, packaging, testing or manufacture.

Based upon studies carried out using other amino-acid based emulsifiers, it is believed that the neutralized amino acid ester emulsifiers of the invention are non-toxic to animals (including humans) and plants, unlike some cationic emulsifiers which may harm wildlife and/or plants when discharged into the environment.

The invention includes methods of increasing the substantivity (adsorbance to a negatively charged substrate, such as hair, skin and nails) of a personal care composition. In some embodiments, the personal care composition may be one that is also natural—i.e., that omits ingredients that are petrochemicals, petrochemical derivatives, materials derived from genetically modified organisms (such as GMO plant materials), and/or any animal materials or derivatives. Accordingly, the composition may be a natural formulation or a conventional formulation, at the formulator's discretion.

The emulsifier of the invention may be delivered to the end formulation ("composition") in any form. For example, it may be carried in a liquid that is initially mixed with one or both of the aqueous or non-aqueous phase(s), or included in an anhydrous formulation. Alternatively, the emulsifier may be in dry or liquid free form, such as a powder, pastille, pellet, bar, grains or granular form that can be delivered to one or both of the aqueous or non-aqueous phase(s) of the composition. If, for example, the emulsifier is provided in dry or liquid free form, it may be desirable to reduce its particle size before its addition to the phase(s) This may be accomplished by any process known in the art, for example, grinding or chopping.

The invention also includes personal care compositions that contain the neutralized amino acid ester; such compositions may contain a non-aqueous phase and an aqueous phase that are emulsified by the ester. The compositions are preferably substantially free of petrochemical or petrochemical derivatives. To form such compositions, an exemplary process may be mixing or otherwise incorporating the neutralized amino acid ester with other ingredients of the composition to formulate the finished product. In some embodiments, the compositions may have a final pH within the upper, more neutral range, e.g., pH of about 5, about 6, and about 7.

In an exemplary hair conditioner base formulation, the neutralized amino acid ester is mixed with fatty alcohol and an emollient and is warmed to about 75° C. to about 85° C. This mixture is then added to hot water and allowed to cool slowly with agitation. In such compositions, the neutralized amino acid ester of the invention serves multiple roles—it emulsifies the aqueous and non-aqueous phases of the invention, it increases the substantively of the personal care composition to skin, hair or nails, and it conditions/lubricates the surfaces of the hair, skin or nail substrates to which it is applied.

The composition of the invention may be formulated to be any type of personal care composition, cosmetic, or pharmaceutical delivery formulation (for example, to deliver therapeutic agents to the skin or gums, or mucous membranes).

Other suitable compositions may include a hair detergent, hair cream conditioner, shampoo, rinse, conditioning shampoo, hair lotions, hair treatment, hair cream, hair spray, hair liquid, hair wax, hair-styling preparation, permanent wave liquids, hair colorant, acidic hair colorant, hair manicure, glaze, skin lotion, milky lotion, face wash, makeup remover, cleansing lotion, emollient lotion, nourishing cream, emollient cream, massage cream, cleansing cream, body shampoo, hand soap, bar soap, shaving creams, sunscreen, sunburn treatment, deodorants, makeup removing gel, moisture gel, moisture essence, UV exposure-preventing essence, shaving foam, face powder, foundation, lipstick, blush, eyeliner, wrinkle and anti-aging cream, eye shadow, eyebrow pencils, mascara, mouthwash, toothpaste, an oral care composition, a skin cleansing composition, a textile cleansing compositions, a dish cleaning composition, a hair or fur cleansing composition, a deodorant or antiperspirant, a cosmetic, a hair styling composition, a skin moisturizer, a skin conditioner, a hair conditioner and a nail conditioner.

The emulsifiers of the invention may be incorporated into compositions that are impregnated within woven or non-woven textiles such as personal wipes or towelettes, baby wipes, makeup removal towelettes, leather wipes, hard surface wipes, diapers, incontinence pads, feminine hygiene products, nursing pads, toilet paper, and facial tissues.

They may also be used in textile treatment compositions (such as fabric cleansers, fabric softeners, ironing treatments) and leather and/or faux leather treatments (cleaners, wipes, conditioners, etc.)

The compositions may include various additives, as are known in the art. Suitable additives include various anionic surfactants, cationic surfactants, amphoteric surfactants, nonionic surfactants, waxes, other oils and fats and derivatives thereof, fatty acid esters of varying chain lengths, synthetic oils and fats, polymers, alcohols, polyhydric alcohols, extracts useful for providing fragrance, amino acids, nucleic acids, vitamins, hydrolyzed proteins and derivatives thereof, glycerine and derivates thereof, enzymes, anti-inflammatory and other medicaments, microbiocides, anti-fungals, antiseptics, antioxidants. UV absorbers, dyes and pigments, sunscreen active agents, chelating agents, sweat retardants, oxidizers, pH balancing agents, glyceryl monoesters, moisturizers, peptides and derivatives thereof, anti-aging actives, hair growth promoters, anti-cellulite actives and the like acceptable for use in formulations for human use. Others include EDTA, glutamic acid, glycerine, panthenol, stearyl alcohol, cetyl alcohol, cyclomethicone, dimethicone, pH adjustment additives, and preferably a water base. In an embodiment, it may be preferred that he sold cationic emulsifier in the composition is the emulsifier of the invention.

Because the emulsifier is substantive to negatively charges substrates, it can be used as an additive in an emulsion or non emulsion composition in methods to increase the substantivity of the composition. Such increase can be measured by comparison of the substantivity of an "identical composition" (i.e., on that contains the same ingredient in the same amount, but for the absence of the emulsifier of the invention) to the substantivity of a composition of the invention to the same substrate. Such comparison may be a relative assessment (in a test carried out by trained individuals applying the compositions to their skin) or a quantitative assessment carried out using analytical methods (e.g., measurement of amount of composition on substrate).

Other methods that are included within the scope of the invention include methods of conditioning the hair and/or skin by applying the personal care compositions described above. It may be desirable that the composition is in the form of an oil-in-water, water-in-oil, or multiple emulsion, but can also be in a form of, for example, creams, lotions, solutions, gels, pastes, mousses, sprays, anhydrous oils, and combinations thereof. The proportion of the neutralized amino acid ester used in the hair condition composition is preferably from about 0.1 to about 10.0 weight percent, and more preferably from about 0.25 to about 5.0 weight percent.

The compositions may contain a single neutralized amino acid ester or more than one, for example, a combination of BAE and OAE may be used.

Also included are methods of forming an emulsion that includes incorporating the amino acid ester of the invention into a mixture containing at least an aqueous phase and non-aqueous phase.

EXAMPLES

In some of the following examples the formulations/compositions are evaluated for "skinfeel" attributes by individuals trained to carry out such evaluations "Skin feel" is a term of art encompassing the aesthetic characteristics the consumer observes/feels when applying a topical product Within the concept of skinfeel, a standard lexicon has developed to describe the step in the process of topical application when the aesthetic property is observed and to describe the specific observation or feeling.

For example, if a skin cream is packaged in a wide mouth canister, the user must remove the product using a finger or fingers for application to the skin. The term to describe this step is "pick-up." Similarly, sensory characteristics that the individual observes when the product is first applied to the skin are observed at "initial feel". Exemplary terms to describe "initial feel" include "light," "rich," "elegant," and "slippery" Sensory characteristics that the individual observes during the process of rubbing the product into the skin until drying can be identified qualitatively as "absorbency" and/or "play time." For example, a product which rapidly dries or seems to disappear quickly would have "high" absorbency and "short" play time. After the product dries, the residual feeling that the consumer experiences is known as the "after-feel." Exemplary terms used to describe this may be "low," "smooth," "emollient," "silky," "powdery," "waxy." "unctuous," "oily," "greasy," "tacky," and/or "waxy." The individuals who evaluated the compositions of the example were trained in the correct and property use of these terms to maintain consistency of the results.

Example 1

Synthesis of Brassicyl Aminolaurate Esylate. A Cationic Emulsifier of the Invention To a one liter round bottom flask affixed with vapor column, total condenser, nitrogen sparge and agitator, about 1.2 moles of Brassicyl alcohol and about 1 mole of 12-aminolauric acid were charged. The *Brassica* alcohol used was a mixture of straight chain saturated fatty alcohols comprising palmityl ($C_{16}$), stearyl ($C_{18}$), arachidyl ($C_{20}$), and behenyl ($C_{22}$) alcohols derived from hydrogenated high erucic acid rapeseed (HEAR) oil. The typical weight percentages of each alcohol in the fatty alcohol mixture are about 3 wt. % palmitic, about 40 wt. % stearyl, about 10 wt. % arachidyl, and about 47 wt. % behenyl. These percentages can vary based upon seasonality, and varietal of rapeseed oil used as the parent vegetable source. The mixture was warmed to about 90° C. with stirring, and about 1 mole of ethanesulfonic acid was added dropwise over about a twenty-minute period. The mixture was then heated to 140° C. and was held for about 16 hours.

The mixture was then cooled to 90° C. and the excess of ethanesulfonic acid was neutralized by adding about 0.03 moles of sodium carbonate dissolved in about 6 grams of water. The mixture was then dried under hard vacuum for about one hour. The mixture was then cooled to about 90° C. and was flaked off, yielding a pale yellow solid product.

The amine value of the material was determined through the use of titration with base using a Metrohm Titrando 808 automatic titrator with Tiamo software (Metrohm USA, (Riverview, Fla. USA). In the method, a sample was weighed and dissolved in un-neutralized denatured ethanol. The mixture was then titrated with dilute sodium hydroxide to the appearance of an endpoint. The value found is 82 mg KOH/g. This was compared to the calculated theoretical amine number of 83 and the % conversion was determined which is approximately 100%.

The infrared spectrum was determined using a Perkin-Elmer Spectrum 100 FT-IR spectrophotometer (Perkin Elmer. Waltham Mass., USA) fitted with a Pike MIRacle ATR (Attenuated Total Reflectance) accessory with ZnSe crystal (Pike, Madison Wis., USA). The spectrum is displayed in FIG. 1. The melting point was determined using an SRS (Stanford Research Systems, Inc. Sunnyvale, Calif., USA) EZMelt automated melting point apparatus and was found to be 83° C.

The pH was determined by dispersing the product at a level 10 wt % in water with heat and agitation, then allowing the dispersion to cool. The pH of the material was measured using a Schott Lab 860 pH meter affixed with an IoLine 1L-pHT-AI 70MF-BNL-N electrode (SI Analytics GmbH, College Station, Tex., USA). It was determined to be 6.4.

Example 2

Preparation of Exemplary Emulsifiers of the Invention

Additional emulsifiers within the scope of the invention were prepared and analyzed using the general methods described in Example 1, and the properties are summarized in Table 1.

TABLE 1

| Ester | Amino Acid | Fatty Alcohol | Actual Amine Value (mg KOH/g) | Theoretical Amine Value (mg KOH/g) | Conversion (%) | Melting Point (° C.) | pH (10% aqueous) |
|---|---|---|---|---|---|---|---|
| Octyldodecyl aminolaurate esylate (OAE) | 12-aminolauric | isostearyl | 98.0 | 95.4 | 97.4 | 38 | 5.6 |
| Isosteryl aminolaurate esylate (IAE) | 12-aminolauric | octyldodecyl | 89.1 | 90.7 | 101.8 | 44 | 6.0 |

Figure 2:
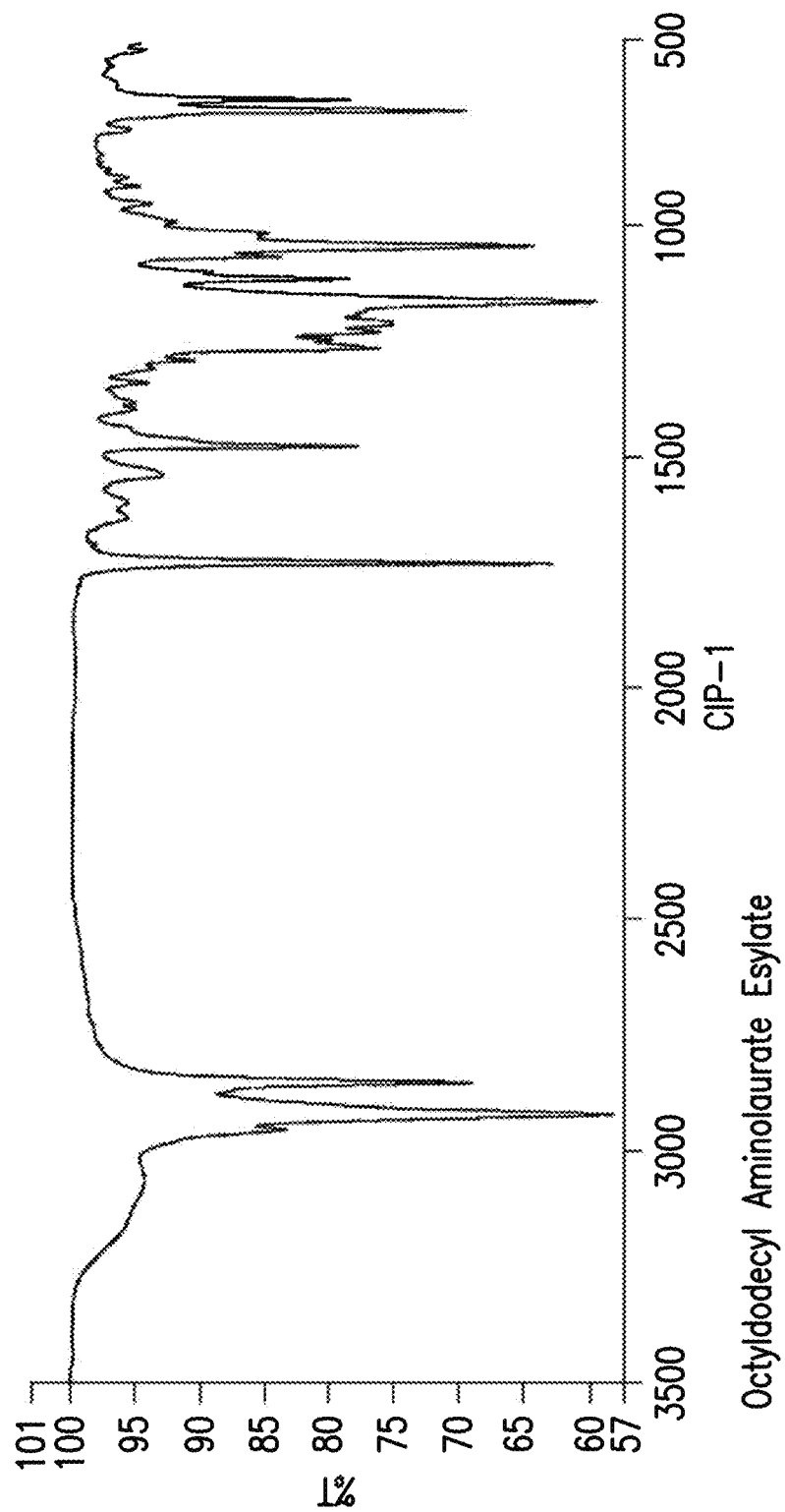
FIG. 2 is an infrared spectrum of an alternative embodiment of the emulsifier of the invention.
Figure 3:
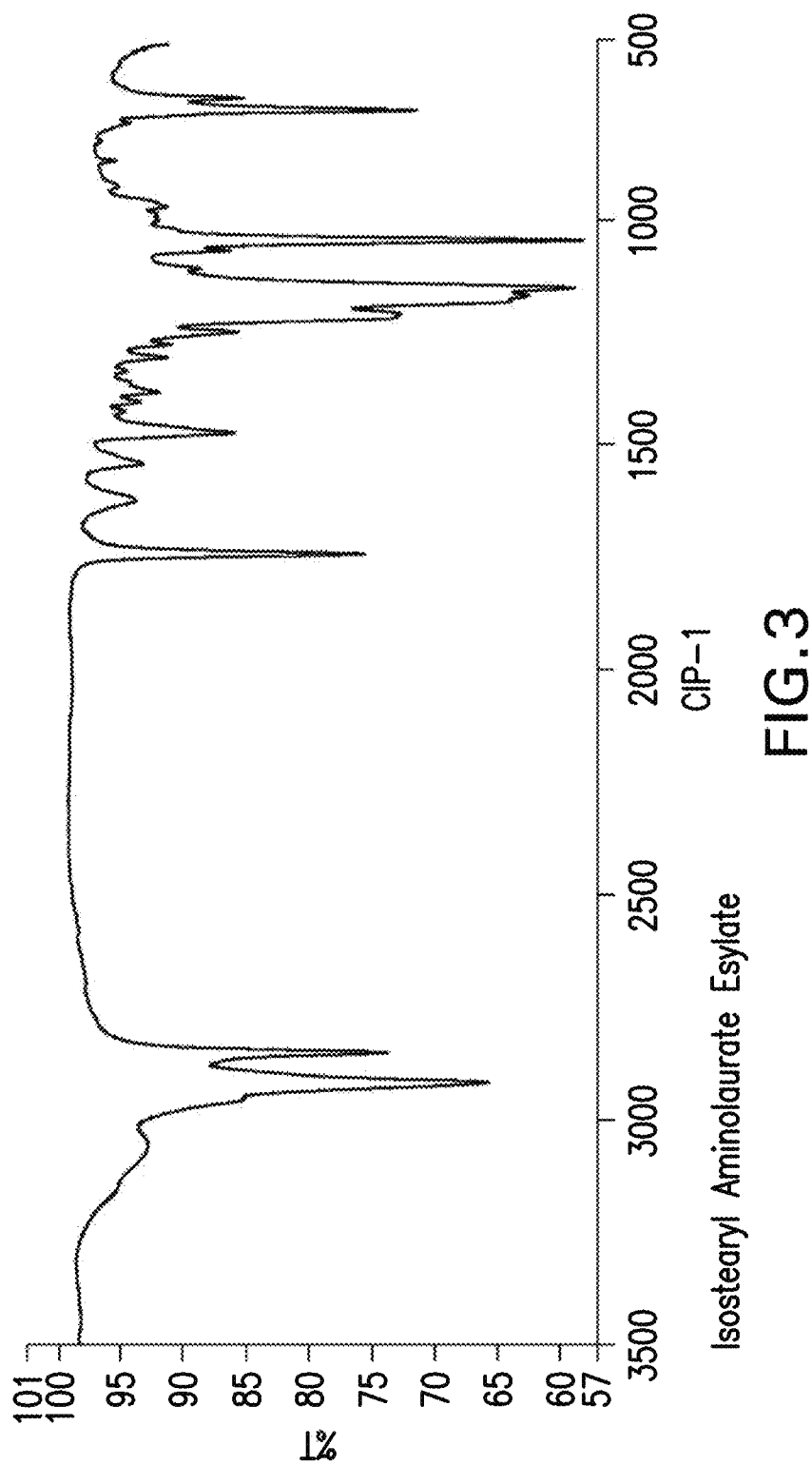
FIG. 3 is an infrared spectrum of an additional alternative embodiment of the emulsifier of the invention.

The infrared spectrum of each of OAE and IAE was determined using a Perkin-Elmer Spectrum 100 FT-IR spectrophotometer (Perkin Elmer, Waltham Mass., USA) fitted with a Pike MIRacle ATR (Attenuated Total Reflectance) accessory with ZnSe crystal (Pike, Madison Wis., USA). The spectrum of each OAE and IAE are displayed in FIGS. 2 and 3, respectively.

Example 3

Activity of the Emulsifier of the Invention in Higher pH Compositions

The emulsifier of the invention is capable of providing substantivity (and the resultant aesthetic and skin feel benefits) when it is included in compositions having higher pHs (e.g., about 5 to about 8.5 or 9.3) The chemical basis of this capability is because the compositions of the invention maintain a large proportion of their neutralized form at the higher pHs. This property can be evaluated by measuring the quantity of amine groups which remain undissociated at a given pH. Since brassicyl aminolaurate esylate, an emulsifier of the invention, is completely neutralized in its native state, it is fully dissociated and cationic. Exposure to a strong base yields the undissociated, free base form, which exhibits less emulsifier function and less substantivity. Exposure to a strong base yields the undissociated, free base form, which exhibits less emulsifier function and less substantivity.

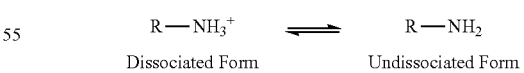

R—NH$_3^+$ ⇌ R—NH$_2$
Dissociated Form     Undissociated Form

In this experiment, the prior art cationic emulsifier brassicyl isoleucinate esylate (disclosed in the Burgo Art) was also evaluated to provide a comparison.

In a 150 mL glass beaker, 0.001184 equivalents of brassicyl isoleucinate esylate was added to 100 grams of water and heated to 80° C., then allowed to cool to about 40-50° C. A translucent dispersion was obtained. As noted, brassicyl isoleucinate esylate is a prior art emulsifier disclosed in the Burgo Art.

In a second 150 mL glass beaker, 0.001666 equivalents of brassicyl aminolaurate esylate, an emulsifier of the instant invention, was added to 100 grams of water and heated to 80° C., then allowed to cool to about 40-50° C. A translucent dispersion was again obtained.

Each of the dispersions was then independently titrated with vigorous stirring with 0.1 N aqueous sodium hydroxide solutions using an automatic titrator Metrohm Titrando 808 automatic titrator with Tiamo software (Metrohm USA, Riverview. Fla., USA). As the solutions are titrated, the amine salt (dissociated form) is transformed to the tree amine (undissociated form.) The dissociated form (cationic) is the desired form. The results obtained are shown in FIGS. 4 and 5.

Figure 4:
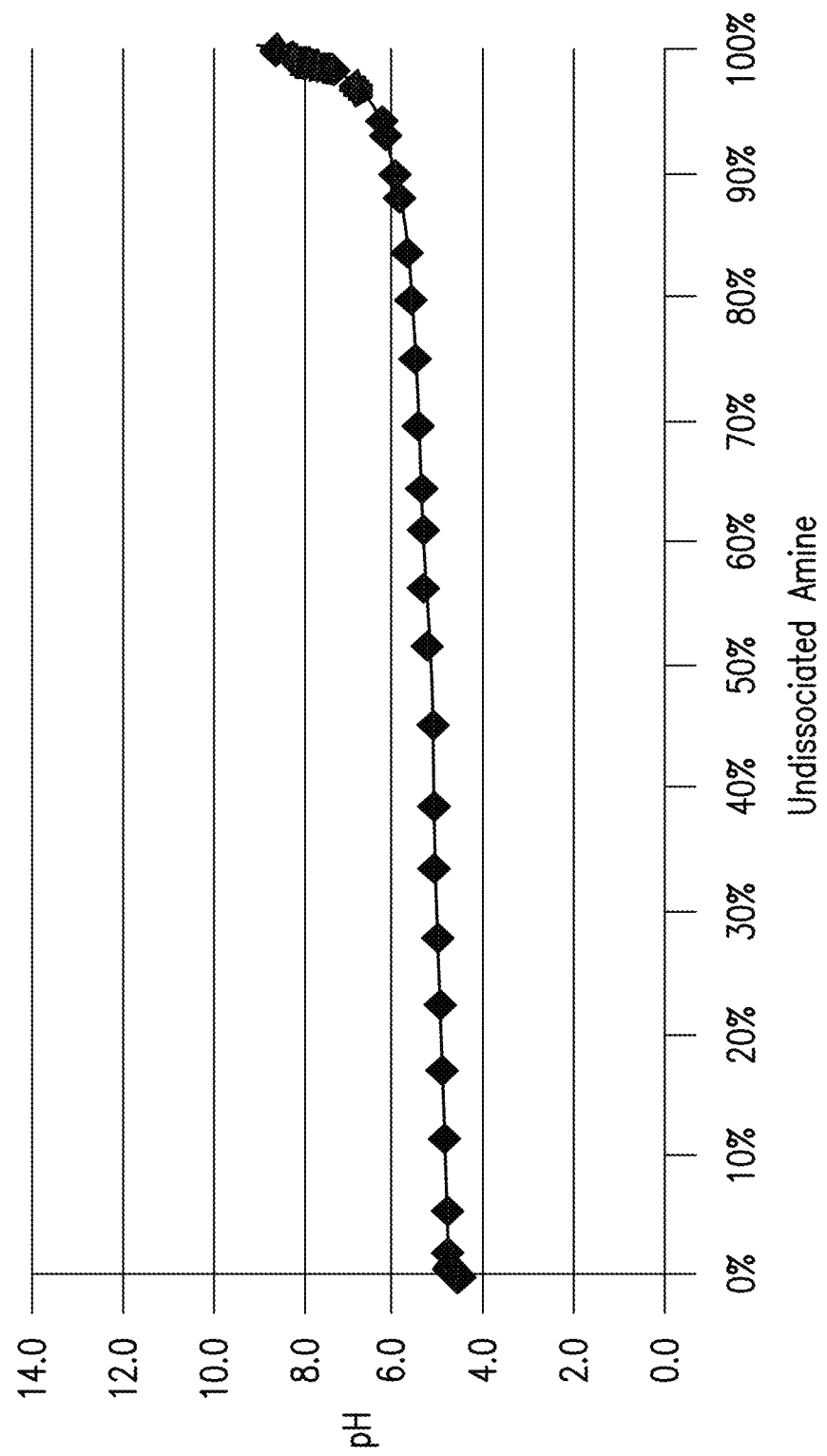
FIG. 4 shows the percent (%) of undissociated amine present in the brassicyl isoleucinate esylate at increasing pH levels.

FIG. 4 shows the percent (%) of undissociated amine present in the brassicyl isoleucinate esylate (BIE) at increasing pH levels. As can be seen in the Figure, the amine of brassicyl isoleucinate esylate is about 90% undissociated at a pH of about 6.

Figure 5:
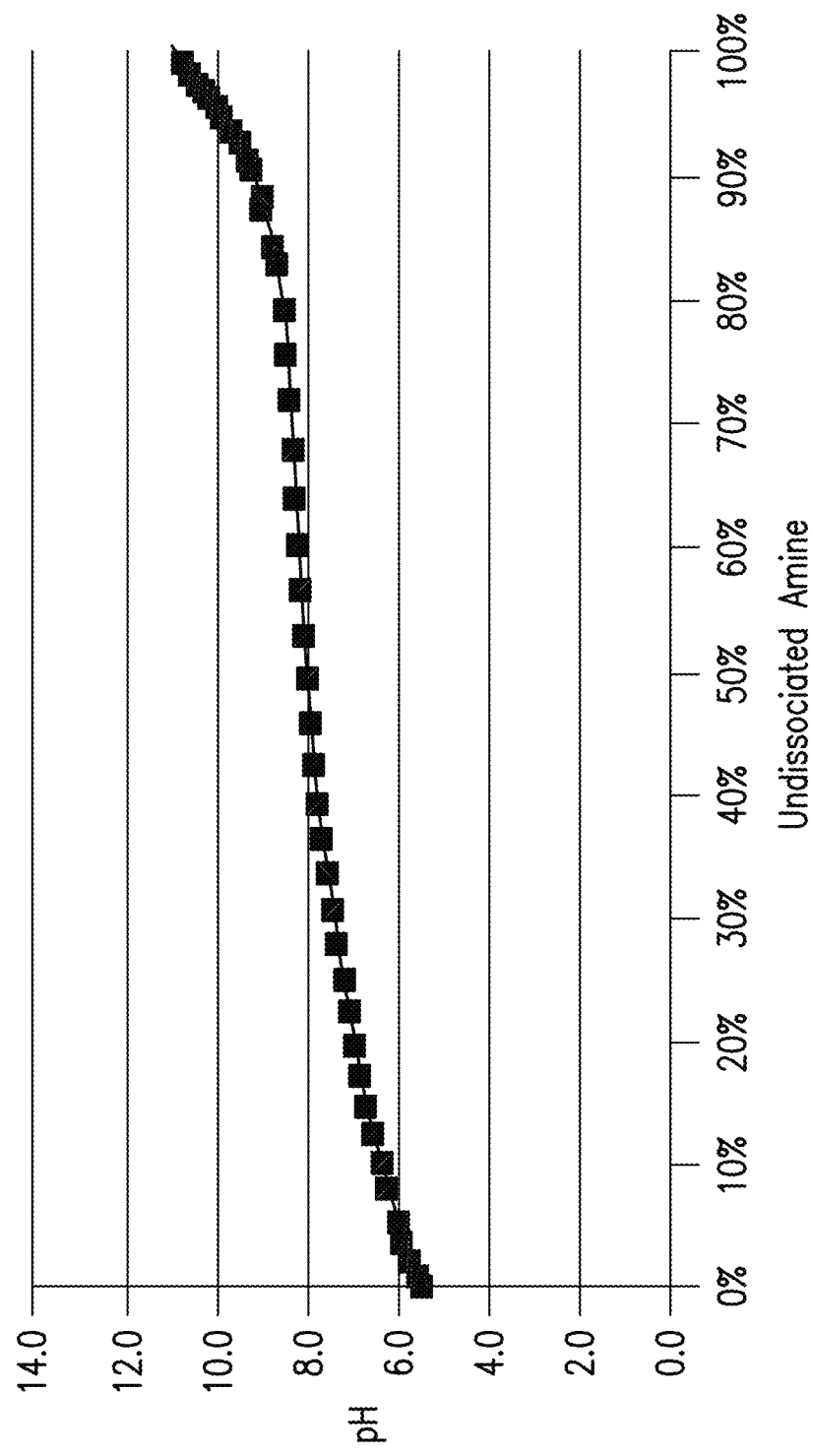
FIG. 5 shows the percent (%) of undissociated amine present in the brassicyl aminolaurate esylate at increasing pH levels.
Figure 6:
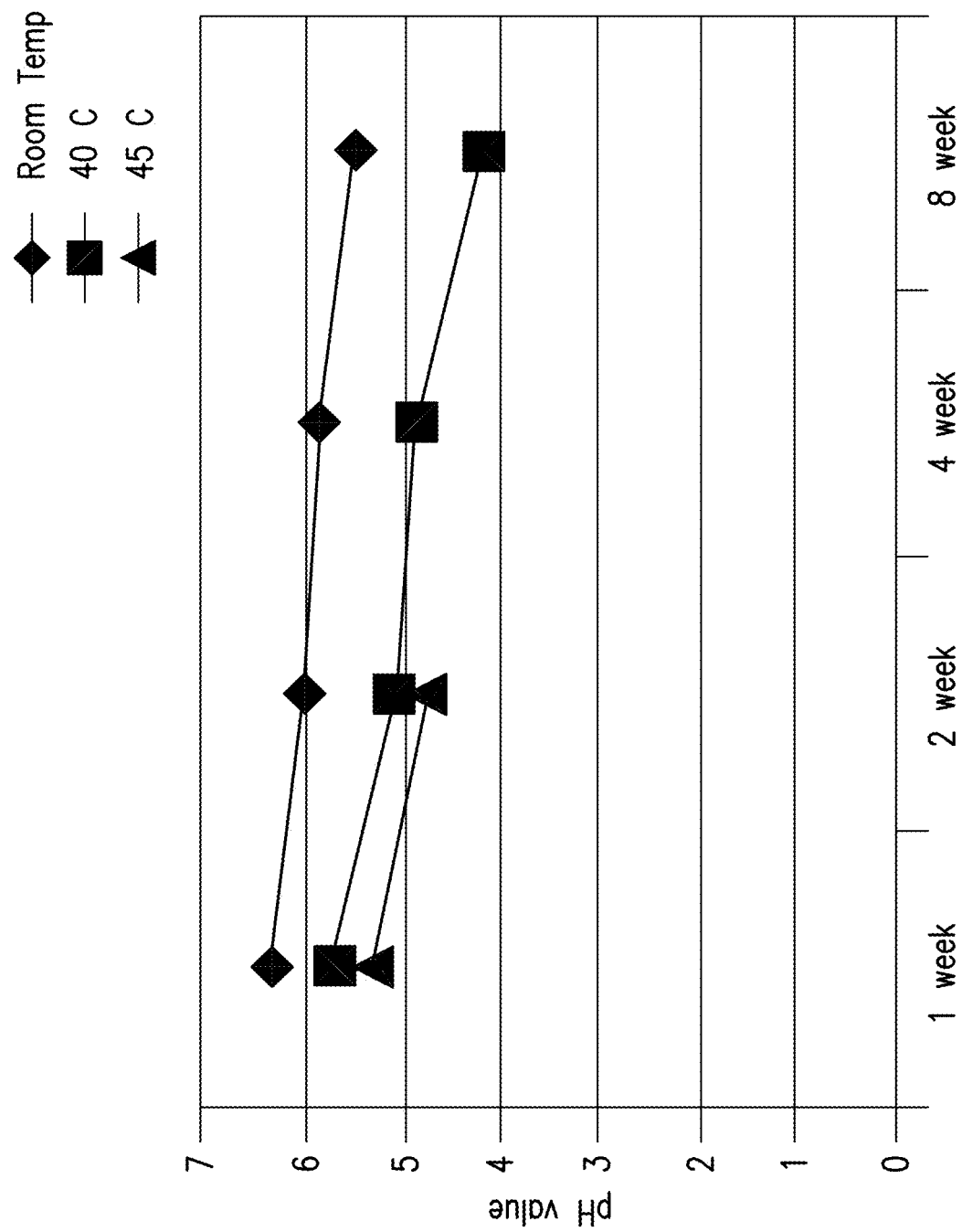
FIG. 6 shows the pH data collected at all temperatures for a deluxe moisturizer composition containing an embodiment of an emulsifier of the invention.
Figure 7:
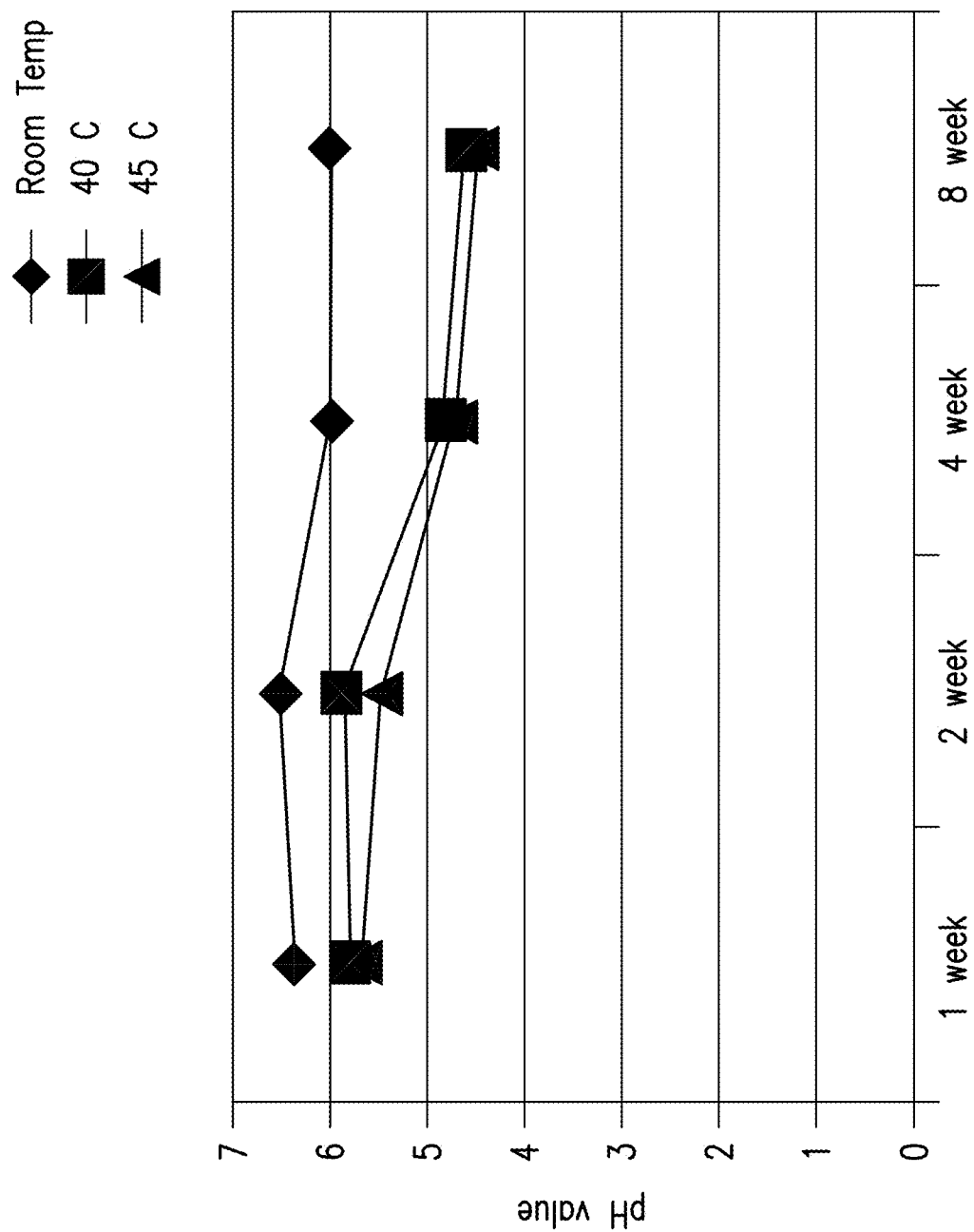
FIG. 7 shows the pH data collected at all temperatures for the sprayable hydrating lotion composition containing an embodiment of an emulsifier of the invention.
Figure 8:
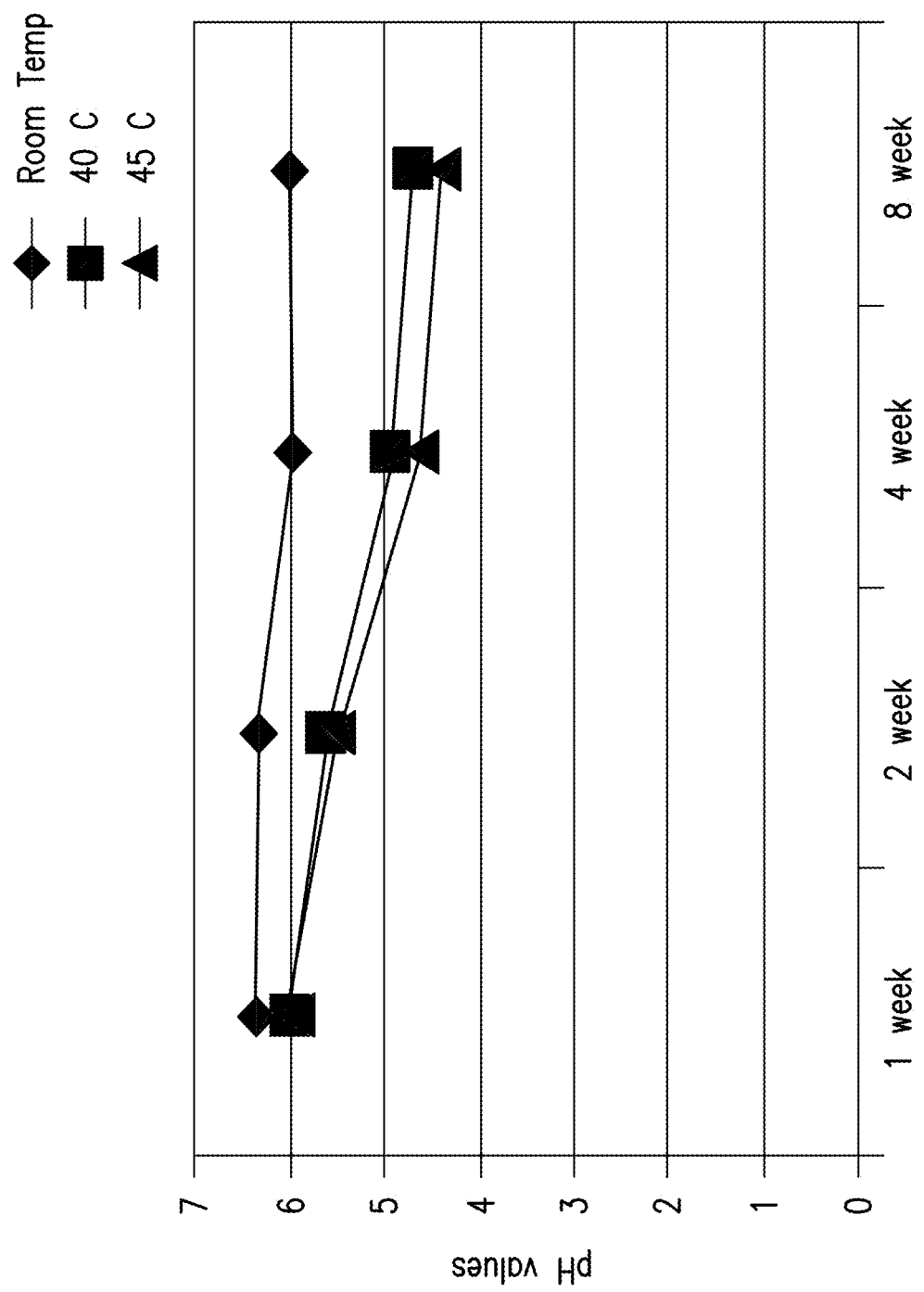
FIG. 8 shows the pH data collected at all temperatures for the baby lotion composition containing an embodiment of an emulsifier of the invention.
Figure 9:
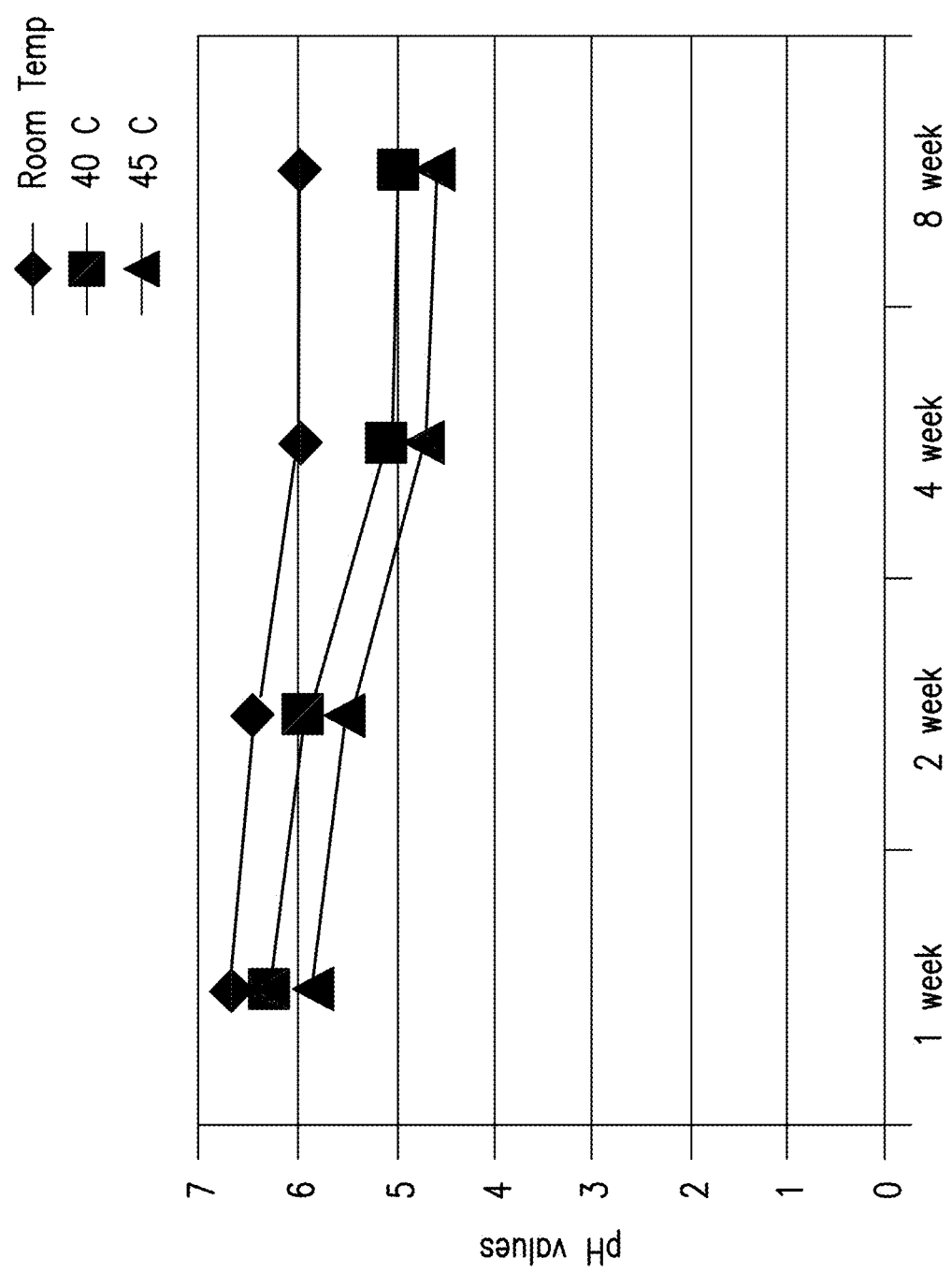
FIG. 9 shows the pH data collected at all temperatures for the body lotion composition containing an embodiment of an emulsifier of the invention.

FIG. 5 shows the percent (%) of undissociated amine present in the brassicyl aminolaurate esylate at increasing pH levels. As can be seen in the Figure, the amine of brassicyl aminolaurate esylate (BAE) is about 90% undissociated at a pH of about 9.

These data establish that the amino acid ester emulsifier of the invention, brassicyl aminolaurate esylate maintains a higher level of the desired dissociated form at a higher pH. For example, with reference to the Figures, at pH 7: (1) BAE (the emulsifier of the invention) remains about 80% cationic at pH 7, and: (2) BIE is essentially 100% undissociated (non-cationic) at pH 7. This is because the pKa of BAE is higher than that of BIE. This ability to maintain cationic form at higher pHs may be desirable in the context of certain type of products, which may exists at higher pH levels.

Example 4

Natural Hair Care Formulation Exhibiting Increased Substantivity to Hair

The following ingredients were mixed together

| Ingredients (INCI Name) | % wt/wt |
|---|---|
| Water | 87.00 |
| Brassicyl Aminolaurate Esylate | 2.00 |
| Cetyl Alcohol | 5.00 |
| Caryloyl Glycerin/Sebacic Acid Copolymer (and) Diheptyl Succinate | 5.00 |
| Glyceryl Caprylate (and) Glyceryl Undecylenate | 1.00 |
| Citric Acid | Q.S. |
| Total | 100.00 |

The pH of the end formulation was determined to be about 6 using an Thermo Orion model 420A pH meter (Thermo Orion, Beverly, Mass., USA) equipped with a Metrohm Unitrode glass electrode model 6.0259.100 (Metrohm USA, Riverview, Fla., USA). The system was calibrated with aqueous buffers, and the determination was made by simply immersing the electrode in the emulsion at room temperature until a stable reading was obtained.

The conditioning behavior of the hair conditioner was evaluated by first preparing two hair tresses comprising virgin brown Caucasian hair by washing with a copious quantity of sodium laureth sulfate solution, then rinsing with copious amounts of water until clean. One tress of wet hair was then treated with the conditioner of the invention, while a second tress was treated with a conditioner made with the emulsifier of the Burgo art. The feeling of the wet hair with each conditioner still on the hair was evaluated by trained individuals. The individuals reported that although the conditioner of the Burgo art provided good slip, the a very high degree of slip was felt when the inventive conditioner was evaluated. By "slip," it is meant that the hands move easily upon the hair surface when massaging the conditioner in, which is a highly desirable benefit. The tresses were then allowed to dry, and the tress treated with the inventive conditioner exhibited a soft, smooth feel with no frizz and minimal fly-away when compared tactily and visually to untreated hair.

Example 5

Preparation of a Deluxe Moisturizer Containing the Emulsifier of the Invention

A deluxe moisturizer was prepared to include an embodiment of the emulsifier of the invention, BAE. The BAE was prepared as in Example 1. The ingredients in the table below were combined together in the amounts shown therein. The resultant emulsion composition was suitable for commercial distribution as a deluxe moisturizer.

| Ingredient (INCI Name) | % W/W |
|---|---|
| Deionized Water | 56.85 |
| Glycerin | 5.00 |
| L-Arginine | 0.15 |
| Brassicyl Aminolaurate Esylate | 3.53 |
| *Brassica* Alcohol | 8.47 |
| Caprylic/Capric Triglyceride | 25.00 |
| Glyceryl Caprylate | 1.00 |
| Total | 100.00 |

The pH of the end formulation was determined to be about 6.6 using the same apparatus and method described previously. The viscosity was measured at room temperature using a Brookfield model RVT rotary viscometer at 10 rpm using spindle C (Brookfield, Middleboro, Mass., USA, and a value of 22,000 centipoise (cP) was obtained.

In subjective testing by trained individuals, upon application to the skin, the skin feeling was described as being "rich" with "long play time upon initial application ("initial feel") The skin was left looking "dewy" and a "skin plumping" effect was observed visually.

Example 6

Preparation of a Sprayable Hydrating Lotion Containing the Emulsifier of the Invention A sprayable hydrating lotion was prepared to include an embodiment of the emulsifier of the invention, BAE. The BAE was prepared as in Example 1. The ingredients of the table below were combined together in the amounts shown therein. The resultant emulsion composition was suitable for commercial distribution as a sprayable hydrating lotion.

| Ingredients (INCI Name) | % W/W |
|---|---|
| Deionized Water | 84.30 |
| Glycerin | 5.00 |
| L-Arginine | 0.20 |
| Glyceryl Caprylate | 1.00 |
| Brassicyl Aminolaurate Esylate | 1.62 |

-continued

| Ingredients (INCI Name) | % W/W |
|---|---|
| Brassica Alcohol | 3.88 |
| Caprylic/Capric Triglyceride | 4.00 |
| Total | 100.00 |

The pH of the end formulation was determined to be about 6.6 using the same apparatus and method described previously. The viscosity was measured at room temperature using the same apparatus of Example 5. A value of 2,000 cP was obtained.

In subjective testing by trained individuals, upon application to the skin, the skin feeling was described as being "fluid" and "watery" upon initial application ("rub-in," "initial feel,") and then "smoothing" and "hydrated" after the formulation had dried and absorbed in ("after-feel.")

Example 7

Preparation of a Natural Baby Lotion

A natural, skin-moisturizing baby lotion was prepared to include an embodiment of the emulsifier of the invention, BAE. The BAE was prepared as in Example 1. The ingredients of the table below were combined together in the amounts shown therein. The resultant emulsion composition was suitable for commercial distribution as a baby lotion.

| Ingredients (INCI Name) | % W/W |
|---|---|
| Deionized Water | 80.25 |
| Glycerin | 2.00 |
| L-Arginine | 0.25 |
| Brassicyl Aminolaurate Esylate | 2.35 |
| Brassica Alcohol | 5.65 |
| Sunflower Oil | 4.00 |
| Glyceryl Caprylate | 1.00 |
| Heptyl Undecylenate | 4.00 |
| Fragrance | 0.50 |
| Total | 100.00 |

The pH of the end formulation was determined to be about 6.6 using the same apparatus and method described previously in Example 5. The viscosity was measured at room temperature using the same apparatus described previously, and a value of 13,000 cP was obtained.

In subjective testing by trained individuals, upon application to the skin, initial the skin feeling was described as being "fast absorbing" with an instant "skin softening" after-feel.

Example 8

Preparation of a Silky-Feeling Body Lotion

A natural body lotion was prepared to include an embodiment of the emulsifier of the invention, BAE. The BAE was prepared as in Example 1. The ingredients of the table below ere combined together in the amounts shown therein. The resultant emulsion composition was suitable for commercial distribution as a body lotion

| Ingredients (INCI Name) | % W/W |
|---|---|
| Deionized Water | 76.95 |
| Glycerin | 5.00 |
| D-Panthenol | 0.10 |
| Allantoin | 0.10 |
| L-Arginine | 0.25 |
| Brassicyl Aminolaurate Esylate | 2.35 |
| Brassica Alcohol | 5.65 |
| Dipentaerythrityl Hexa C5-9 Acid Esters | 3.00 |
| Glyceryl Caprylate | 1.00 |
| Caprylic/Capric Triglyceride | 5.00 |
| D-Alpha-Tocopherol | 0.10 |
| Fragrance | 0.50 |
| Total | 100.00 |

The pH of the end formulation was determined to be about 6.7 using the same apparatus and method described previously. The viscosity was measured at room temperature using the same apparatus described previously, and a value of 25,000 cP was obtained.

In subjective testing by trained individuals, upon application to the skin, the skin feeling was described as being "silky" and "cooling" during rub-in, with a "satiny" smooth after-feel.

Example 9 pH Stability Testing of Compositions Containing the Emulsifier of the Invention

Four personal care compositions of varying types were prepared:

(i) a deluxe moisturizer, prepared as set forth in Example 5;

(ii) a sprayable hydrating lotion, prepared as set forth in Example 6;

(iii) a natural baby lotion, prepared as set forth in Example 7; and (iv) a silky-feeling body lotion, prepared as set forth in Example 8.

Sufficient quantities of each formulation were prepared to fill three transparent four ounce glass jars (three samples of each ["sets"]) and were sealed using plastic caps. The first set of each of the four formulations were held in a laboratory at room temperature in the presence of light. The second set was placed in a stability oven set at 40+−2° C. The third set was placed in a stability oven set at 45+/−2° C. The stability ovens shield the formulations from light.

Each of the samples were allowed to cool to room temperature and the pH was evaluated using the method described previously after intervals of one, two, four, and eight weeks of storage under the stability test condition. The results are shown in FIGS. 6, 7, 8, and 9B. The data obtained was evaluated to determine the pH drift of each of the formulations.

Some pH drift is typical even in stable emulsions. However, substantial drift over a relatively short period of time is indicative of an unstable emulsion. The results show that emulsions made using the emulsifier of the invention experience minimal pH drift, even under accelerated stability conditions.

Example 10

Use of Octyldodecl Aminolaurate Esylate in a Deluxe Moisturizer Formulation

A deluxe moisturizer was prepared to include an embodiment of the emulsifier of the invention, octyldodecyl aminolaurate esylate (OAE.) The OAE was prepared as in Example 2. The ingredients set out in the table below were combined together in the amounts shown therein. The resultant emulsion composition was suitable for commercial distribution as a deluxe moisturizer

| Ingredient (INCI Name) | % W/W |
| --- | --- |
| Deionized Water | 56.85 |
| Glycerin | 5.00 |
| L-Arginine | 0.15 |
| Octyldodecyl Aminolaurate Esylate | 3.53 |
| Brassica Alcohol | 8.47 |
| Caprylic/Capric Triglyceride | 25.00 |
| Glyceryl Caprylate | 1.00 |
| Total | 100.00 |

The pH of the end formulation was determined to be about 6.5 using the same apparatus and method described previously. The viscosity was measured at room temperature using a the method described and a value of 2,000 centipoise (cP) was obtained.

In subjective testing by trained individuals, upon application to the skin, the skin feeling was described as being "thin" and "milky" but also, and has a long "play time" during rub-in considering its viscosity. The after-feel was oleaginous which is highly desirable in applications such as anti-aging skin creams.

Example 11

Use of Isostearyl Aminolaurate Esylate in a Deluxe Moisturizer Formulation

A deluxe moisturizer was prepared to include an embodiment of the emulsifier of the invention, isostearyl aminolaurate esylate (IAE.) The IAE was prepared as in Example 2. The ingredients as set out in the table below were combined together in the amounts shown therein. The resultant emulsion composition was suitable for commercial distribution as a deluxe moisturizer.

| Ingredient (INCI Name) | % W/W |
| --- | --- |
| Deionized Water | 56.85 |
| Glycerin | 5.00 |
| L-Arginine | 0.15 |
| Isostearyl Aminolaurate Esylate | 3.53 |
| Brassica Alcohol | 8.47 |
| Caprylic/Capric Triglyceride | 25.00 |
| Glyceryl Caprylate | 1.00 |
| Total | 100.00 |

The pH of the end formulation was determined to be about 6.6 using the same apparatus and method described previously. The viscosity was measured at room temperature using a the method described and a value of 54,000 centipoise (cP) was obtained.

In subjective testing by trained individuals, the formulation formed peaks and had a silky feel upon pick-up and rub-in. The after feel as unctuous, which is desired in certain applications.

While it has been shown and described several embodiments in accordance with the invention and use thereof, it is understood that the same is not limited thereto, but is susceptible to many changes and modifications to one possessing ordinary skill in the art, and therefore we do not wish to be limited to the details shown and described herein, but intend to cover all such modifications as are encompassed by the scope of the appended claims.

I claim:

1. A method of increasing the substantivity of a composition to a negatively charged substrate comprising preparing a composition comprising at least one phase and an effective amount of an amino acid ester selected from the group consisting of octyldodecyl aminolaurate esylate, brassicyl aminolaurate esylate and isostearyl aminolaurate esylate that is a reaction product of a neutralized amino acid consisting of 12-aminolauric acid esterified with a fatty alcohol selected from the group consisting of octylododecyl alcohol, Brassica alcohol, and isostearyl alcohol, and applying the composition to a surface of hair, nails, or skin of a human, wherein the composition exhibits increased substantivity to a negatively charged surface relative to the substantivity of an identical composition that does not contain the amino acid ester and wherein the composition has a pH of 6.0 to 9.3.

2. The method of claim 1, wherein the composition is an emulsion.

3. The method of claim 1, wherein the neutral amino acid is obtained from vegetable matter.

4. A method of preparing an emulsified composition that exhibits substantivity when applied to a negatively charged substrate comprising combining an effective amount of an emulsifier, a first phase, and a second phase, wherein the emulsifier is an effective amount of an amino acid ester selected from the group consisting of octyldodecyl aminolaurate esylate, brassicyl aminolaurate esylate and isostearyl aminolaurate esylate that is a reaction product of a neutralized amino acid consisting of 12-aminolauric acid esterified with a fatty alcohol selected from the group consisting of octylododecyl alcohol, Brassica alcohol, and isostearyl alcohol; and the amine group of the amino acid is neutralized with an acid prior to esterification, wherein the emulsifier serves to emulsify the first and the second phases to form an emulsion.

5. The method of claim 4, wherein the first phase is an aqueous phase and the second phase is a non-aqueous phase.

6. A method of emulsifying a personal care composition having an aqueous phase and a non-aqueous phase comprising incorporating the aqueous phase and a non-aqueous phase with each other in the presence of an effective amount of the emulsifier of claim 4.

7. The method of claim 6, wherein each of the aqueous phase and the nonaqueous phase is substantially free of petrochemicals and/or derivatives of petrochemical materials.

8. The method of claim 4, wherein the emulsified composition has a pH of 6.0 to 9.3.

* * * * *